United States Patent
Kovach

(10) Patent No.: US 9,522,072 B2
(45) Date of Patent: Dec. 20, 2016

(54) POROUS MATERIALS HAVING A FIBRILLAR MICROSTRUCTURE AND A FRACTURABLE COATING

(71) Applicant: W. L. Gore & Associates, Inc., Newark, DE (US)

(72) Inventor: Larry J. Kovach, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 150 days.

(21) Appl. No.: 14/198,901

(22) Filed: Mar. 6, 2014

(65) Prior Publication Data
US 2014/0277374 A1    Sep. 18, 2014

Related U.S. Application Data

(60) Provisional application No. 61/787,989, filed on Mar. 15, 2013.

(51) Int. Cl.
*A61F 2/06* (2013.01)
*A61F 2/82* (2013.01)
(Continued)

(52) U.S. Cl.
CPC .................. *A61F 2/82* (2013.01); *A61L 27/16* (2013.01); *A61L 27/34* (2013.01); *A61L 27/50* (2013.01);
(Continued)

(58) Field of Classification Search
CPC ...... A61F 2/90; A61F 2/07; A61F 2002/9511; A61F 2/82; A61F 2/844; A61F 2/86; A61L 31/10; B29K 2027/18
(Continued)

(56) References Cited

U.S. PATENT DOCUMENTS 4,877,661 A * 10/1989 House et al. ................ 428/34.9
5,308,664 A    5/1994 House et al.
(Continued)

FOREIGN PATENT DOCUMENTS

EP    0 759 730    2/1999
EP    0 821 648    9/2001
(Continued)

OTHER PUBLICATIONS

International Search Report and Written Opinion for PCT/US2014/021554 mailed Aug. 22, 2014, corresponding to U.S. Appl. No. 14/198,901, 7 pages.

*Primary Examiner* — Katherine M Shi

(57) ABSTRACT

Articles made of a porous material having a fibrillar microstructure of bent fibrils and provided with a fracturable coating whereby the physical size of the article may be changed by the application of force to the article in a direction substantially parallel to a direction of orientation of the fibrils. The application of a tensile force to such an article in a direction substantially parallel to orientation of the bent fibrils results in fracturing of the fracturable material and straightening of the bent fibrils. Methods of making such articles are also described. The articles may include implantable articles such as vascular grafts and stent-grafts; such devices may, for example, be forcibly increased in diameter or in length wherein the force results in fracturing of the coating. One such coated material is porous expanded polytetrafluoroethylene provided with a coating of fluorinated ethylene propylene.

30 Claims, 16 Drawing Sheets

(51) Int. Cl.
    *A61L 27/34*     (2006.01)
    *A61L 27/16*     (2006.01)
    *A61L 27/50*     (2006.01)
    *A61L 31/04*     (2006.01)
    *A61L 31/10*     (2006.01)
    *A61L 31/14*     (2006.01)

(52) U.S. Cl.
    CPC ............ *A61L 27/507* (2013.01); *A61L 31/048* (2013.01); *A61L 31/10* (2013.01); *A61L 31/14* (2013.01)

(58) Field of Classification Search
    USPC ... 623/1.12, 1.13, 1.15, 1.18, 1.2, 1.32, 1.53
    See application file for complete search history.

(56) References Cited

U.S. PATENT DOCUMENTS

| | | | |
|---|---|---|---|
| 5,620,763 A | 4/1997 | House et al. | |
| 5,735,892 A | 4/1998 | Myers et al. | |
| 5,788,626 A * | 8/1998 | Thompson .................. | 623/1.15 |
| 5,800,512 A | 9/1998 | Lentz et al. | |
| 5,843,173 A | 12/1998 | Shannon et al. | |
| 5,899,935 A * | 5/1999 | Ding ............................ | 623/1.53 |
| 5,925,074 A | 7/1999 | Gingras et al. | |
| 5,968,070 A | 10/1999 | Bley et al. | |
| 5,968,091 A * | 10/1999 | Pinchuk et al. ............. | 623/1.16 |
| 6,036,724 A | 3/2000 | Lentz et al. | |
| 6,315,791 B1 | 11/2001 | Gingras et al. | |
| 6,497,722 B1 | 12/2002 | Von Oepen et al. | |
| 6,673,105 B1 | 1/2004 | Chen | |
| 6,780,497 B1 | 8/2004 | Walter | |
| 6,863,686 B2 | 3/2005 | Shannon et al. | |
| 6,878,161 B2 | 4/2005 | Lenker | |
| 6,890,350 B1 | 5/2005 | Walak | |
| 8,062,354 B2 | 11/2011 | Shannon et al. | |
| 2005/0090888 A1 * | 4/2005 | Hines et al. ................. | 623/1.11 |
| 2007/0233270 A1 | 10/2007 | Weber et al. | |
| 2010/0312326 A1 | 12/2010 | Chuter et al. | |
| 2013/0253426 A1 * | 9/2013 | Campbell ............... | A61L 29/16 604/103.02 |

FOREIGN PATENT DOCUMENTS

| | | |
|---|---|---|
| EP | 1 582 181 | 10/2005 |
| WO | 01/45766 | 6/2001 |
| WO | 2004/000375 | 12/2003 |

\* cited by examiner

POROUS MATERIALS HAVING A FIBRILLAR MICROSTRUCTURE AND A FRACTURABLE COATING

FIELD OF THE INVENTION

The present invention relates to porous fibrillated materials that are, during normal use, permanently extendable in at least one dimension by the application of a tensile force.

BACKGROUND OF THE INVENTION

Various commercial articles have been manufactured from porous materials having fibrillar microstructures including various implantable medical devices. Examples of these materials may include porous expanded polytetrafluoroethylene (ePTFE) and stretched polyethylenes and polypropylenes. Articles fabricated from these porous fibrillated materials include fabrics, battery membranes, various filters, electrical insulation and various medical devices including vascular grafts, tissue repair patches, sutures and stent-grafts. Porous materials used to manufacture articles such as these can take the form of, for example, sheets, thin films and tubes. It is known that nominal physical dimensions of some of these articles may be changed (reduced) by applying compressive forces to these materials, particularly in a direction substantially parallel to the predominant direction of the fibrils. Compressive forces applied to these materials result in a decrease in porosity (i.e., an increase in bulk density; a decrease in the volume of void space) as the material is moved into the available void space due to the compressive force. Compressive forces applied to these fibrillar materials in directions substantially parallel to the general directional orientation of the fibrils will result in bending of the previously substantially straight fibrils. The compressed material may then be heated for suitable time and temperature so that the bent form of the fibrils becomes permanent. Fibrillar materials so processed to have these formed bent fibrils are typically extensible by applied tensile force in a direction generally parallel to the directional orientation of the fibrils. Upon release of the tensile force, these materials will typically recover most or all of the extended length. The use of compression to form bent fibrils in fibrillated materials is taught in U.S. Pat. No. 5,308,664 to House and Myers.

It is also known to apply coatings of various materials to fibrillated polymeric substrates for a variety of purposes. Thermoplastic coatings on such substrates are sometimes used as adhesives for bonding together different components of an article. A thermoplastic coating of fluorinated ethylene propylene (FEP) applied to ePTFE, for example, is taught by U.S. Pat. No. 5,735,892 to Myers et al.

For some applications, however, it may be advantageous for a product to remain at the partially or fully extended dimension following release of the extending tensile force. A fracturable coating applied to a porous substrate material having a microstructure of bent fibrils may be used to create an article that can be, during normal use, permanently increased in at least one dimension by the application of a tensile force.

SUMMARY OF THE INVENTION

A coating applied to fibrillated porous materials having bent fibrils is described that allows a size dimension of an article fabricated from such a material to be permanently increased by the application of an extending force. One suitable precursor porous substrate material is ePTFE that has been compressed in a direction substantially parallel to a direction of orientation of the fibrils generally as taught by U.S. Pat. No. 5,308,664 to House and Myers, incorporated by reference herein in its entirety. The coating may be any material that solidifies to provide a material that is fracturable under the deliberate application of a tensile force during normal use of the article (e.g., solvent-based coatings). The coating may be applied before or after bending of the fibrils. Particularly for use with ePTFE substrates, the coating may be, for example, a thermoplastic polymeric material and more particularly may be a thermoplastic fluoropolymer such as FEP.

Coating materials may be applied to one or both surfaces of a porous fibrillated substrate material or alternatively may be impregnated into void spaces of the substrate. Some degree of impregnation may occur with coatings that are applied to the substrate surfaces. Coating materials other than thermoplastic materials may include, for example, various polyimides. The amount of coating material and the coating thickness will need to be determined based on the requirements of the article being manufactured.

Articles made as taught herein may be in the form of sheets, rods, tubes or any other form that may benefit from being made to be extensible in at least one direction. One way of making a sheet article is to take a length of a tube and cut it lengthwise through its wall thickness.

The fibrils of the substrate material are required to be bent, generally as taught by U.S. Pat. No. 5,308,664. The presence of bent fibrils provides the substrate material with extensibility in the direction of orientation of the fibrils; i.e., the length of the material may be extended progressively until the bent fibrils are pulled out to a substantially straight configuration. When a fibrillated porous substrate such as described herein is provided with a suitable fracturable coating (constraining the fibrils in their bent form), it may be extended in the general direction of orientation of the fibrils by the application of an extending force sufficient to fracture the coating material to thereby allow at least one dimension of the material to be extended by straightening of the bent fibrils.

Substrate materials such as ePTFE may be provided with a covering or wrapping of a thin film such as ePTFE film. The film may be joined to a substrate layer so that the predominant direction of orientation of fibrils within the film is oriented in a different direction to the predominant direction of fibrillar orientation of the substrate; likewise, the fibrillar orientations of these two layers may be in the same direction. Such laminates of film and substrate may be provided with bent fibrils in either the substrate layer, the film layer or both layers. It is also apparent that laminates may include multiple layers of film (with individual layers oriented as desired) without a different (from the film) substrate layer. The use of film and substrate laminates is known with ePTFE materials. A particularly useful ePTFE film for the manufacture of articles as described herein is taught by U.S. Pat. No. 5,476,589 to Bacino, incorporated by reference herein in its entirety.

The coated materials described herein are anticipated to be particularly useful for implantable medical devices such as vascular grafts and stent-grafts when it may be desirable for a medical practitioner to be able to permanently increase the length, the diameter or both the length and the diameter of such devices. For length extension, the extending force is a longitudinally oriented tensile force that may be applied by hand. For diameter increases, typically the extending force would be applied by inflation of a catheter balloon within the lumen of a device. While a balloon exerts an outward force in a direction against the wall thickness of a tubular device, that outward force translates into a circumferentially oriented tensile force to cause straightening of circumferentially oriented bent fibrils and fracturing of the fracturable coating material.

Grafts made as described herein can allow for customization of device diameter to match the vessel treatment zone. Tapered vessels may be treated more easily. Risk of infolding of graft material due to an overly large diameter graft being fitted within a smaller vessel is reduced or eliminated, thus providing a substantially wrinkle-free lumen. The number of device sizes required to treat a patient population can be reduced because a given device made as taught herein can be used to treat a larger range of vessel sizes than devices made with more conventional technologies. Various applications of such devices may include stent-grafts for peripheral applications and for aneurismal repair, stent-grafts provided on one or both ends of a vascular graft for dialysis, pediatric shunts and hepatic grafts. It is also noteworthy that the radial force of a self-expanding stent-graft against a vessel wall is minimized by the use the fracturable coating described herein to constrain the self-expanding stent rather than the self-expanding stent being constrained by the vessel.

Any of these graft products may also be provided with therapeutic agents known in the art (e.g., anti-clotting agents). For some applications, a therapeutic agent may be incorporated with the fracturable coating. Other applications may involve the application of a therapeutic agent to an uncoated surface of the fibrillated substrate, e.g., directly to an ePTFE surface.

A method of making such devices (as will be further described) involves the use of a tubular fibrillated substrate (e.g., a longitudinally extruded and expanded ePTFE tube having fibrils that are oriented in a direction substantially parallel to the longitudinal axis of the tube) that has been wrapped with a thin fibrillated film. Wrapping is most easily accomplished by first temporarily placing the substrate tube onto a mandrel. The wrapping is preferably a helical wrap using a film that has been cut into a tape, with the predominant direction of orientation of the fibrillar microstructure of the film being parallel to the length of the tape. The tape will have been provided with a coating of a fracturable material prior to the wrapping step. This fracturable material may also serve as an adhesive to adhere the wrapped tape to the substrate tube, in which case the wrapping will be performed with the coated side of the tape facing the substrate. If the coating is a thermoplastic material, the wrapped substrate tube (still on the temporary mandrel) may be heated sufficiently to cause the coating to melt to an extent to ensure adhesion between the tape and the substrate. The mandrel may be removed following the heating step.

If a longitudinally extensible device is desired, then the substrate tube should be provided with bent fibrils that are primarily longitudinally oriented. If a diametrically extensible device is desired then following the application of the helically wrapped film, the diameter of the device is compacted (i.e., reduced) to cause the circumferentially oriented fibrils of the film to become bent. The compacting force is essentially a compressive force. This compacting may be accomplished prior to or during the above-described heating step. It is also possible to make such a device having both longitudinally and circumferentially oriented bent fibrils that is extensible both longitudinally and horizontally.

An alternative method entails modifying a fibrillated porous material having a microstructure of nodes interconnected by fibrils, by applying compression to the material in a direction parallel to the orientation of the length of the nodes in an amount sufficient to cause buckling and folding of the nodes. This is preferably accomplished in a manner that does not result in macroscopically visible wrinkling of the material. Heat may be applied to the material after the nodes have been folded sufficient to set the form of the folded nodes. Such a material may subsequently be extended in the direction of the length of the nodes back to about its pre-compressed dimension, by the application of a sufficient tensile force.

U.S. Pat. No. 6,336,937 to Vonesh et al. entitled Multi-stage Expandable Stent-Graft teaches a method of making stent-grafts that are self-expanding devices that may be subsequently adjusted to a still larger diameter with a catheter balloon. While the method of this patent is different from the method taught herein, U.S. Pat. No. 6,336,937 is incorporated by reference herein in its entirety.

DETAILED DESCRIPTION OF THE INVENTION

As described above, for the manufacture of extensible medical devices such as vascular grafts and stent-grafts, ePTFE films are preferred for use with ePTFE substrates. A preferred fracturable coating for these ePTFE films (particularly for implantable medical devices) is FEP. The FEP-coated porous expanded PTFE film described herein was made by a process which comprises the steps of:
  a) contacting a porous PTFE film with another layer which is preferably a film of FEP or alternatively of another thermoplastic polymer;
  b) heating the composition obtained in step a) to a temperature above the melting point of the thermoplastic polymer;
  c) stretching the heated composition of step b) while maintaining the temperature above the melting point of the thermoplastic polymer; and
  d) cooling the product of step c).

In addition to FEP, other thermoplastic polymers including thermoplastic fluoropolymers may also be used to make this coated film. The coating on the porous expanded PTFE film may be either continuous (non-porous) or discontinuous (porous) depending primarily on the amount and rate of stretching, the temperature during stretching, and the thickness of the adhesive prior to stretching. The coated films may be easily cut into tapes for wrapping tubular substrates.

The discontinuously FEP-coated porous expanded PTFE film used to construct the devices described herein (unless specifically described otherwise) was of about 0.025 mm thickness. The ePTFE portion of this coated film had a bulk density of about 0.6 g/cc; the film chosen was an ePTFE film made generally as taught by U.S. Pat. No. 5,476,589 to Bacino.

The following scanning electron photomicrographs are provided as an overview of materials chosen to manufacture examples described herein. The images depict these materials at various stages of manufacture of a stent-graft and also illustrate the effects of subsequent balloon expansion on the materials of the completed stent-graft. The photomicrographs are oriented so that the longitudinal axis of the illustrated tubular structure is horizontal when viewing the photomicrographs with the label at the lower edge.

Figure 1:
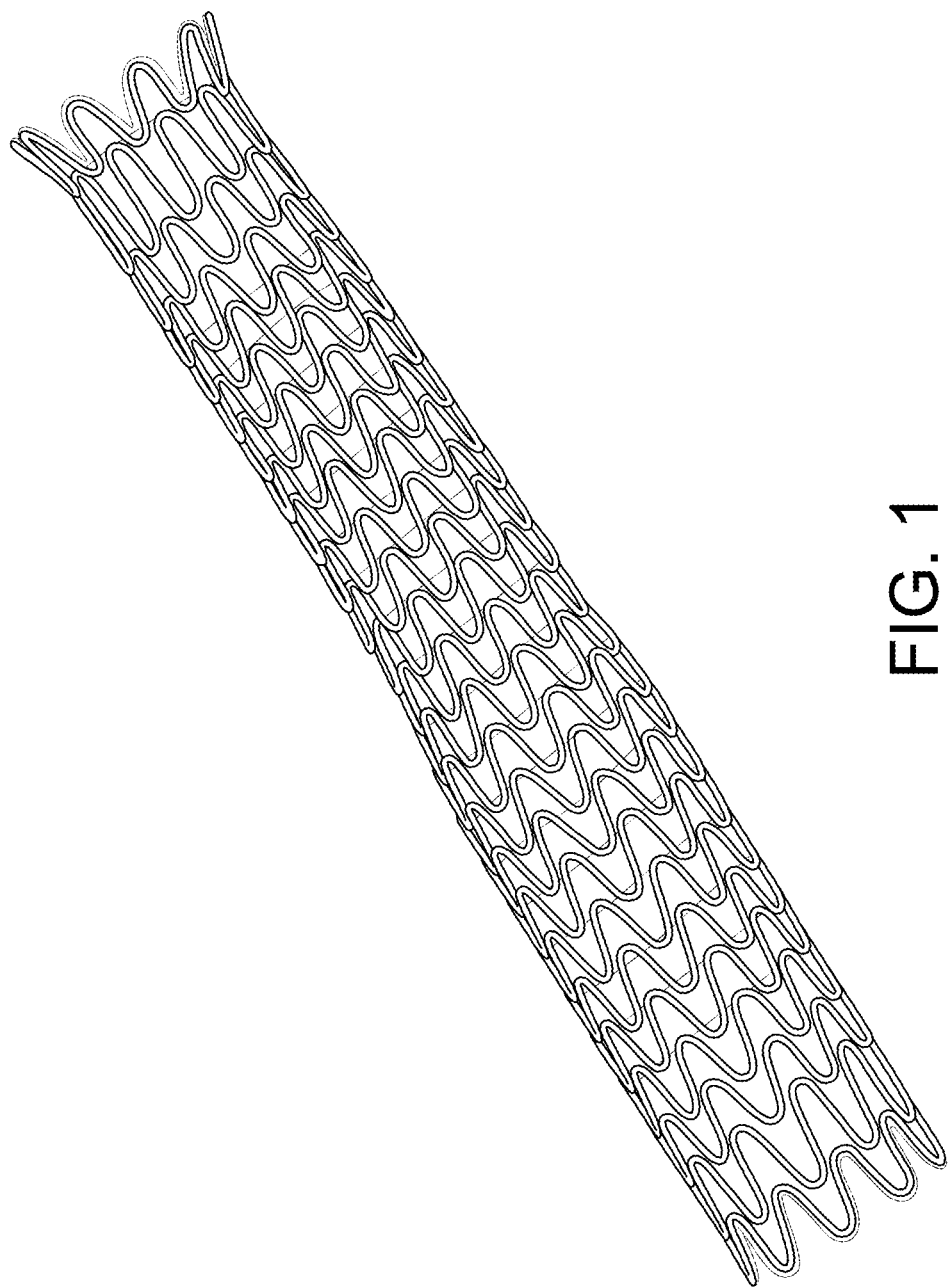
FIG. 1 is a light microscopy photograph of a of a stent-graph of about 5 cm length made as described herein; about one half of the length of the device has been expanded by a catheter balloon from an inside diameter of 4 mm to an inside diameter of 6 mm.

FIG. 1 is a light microscopy photograph of a stent-graph of about 5 cm length made as described herein; about one half of the length of the device has been expanded by a catheter balloon from an inside diameter of 4 mm to an inside diameter of 6 mm.

Figure 2:
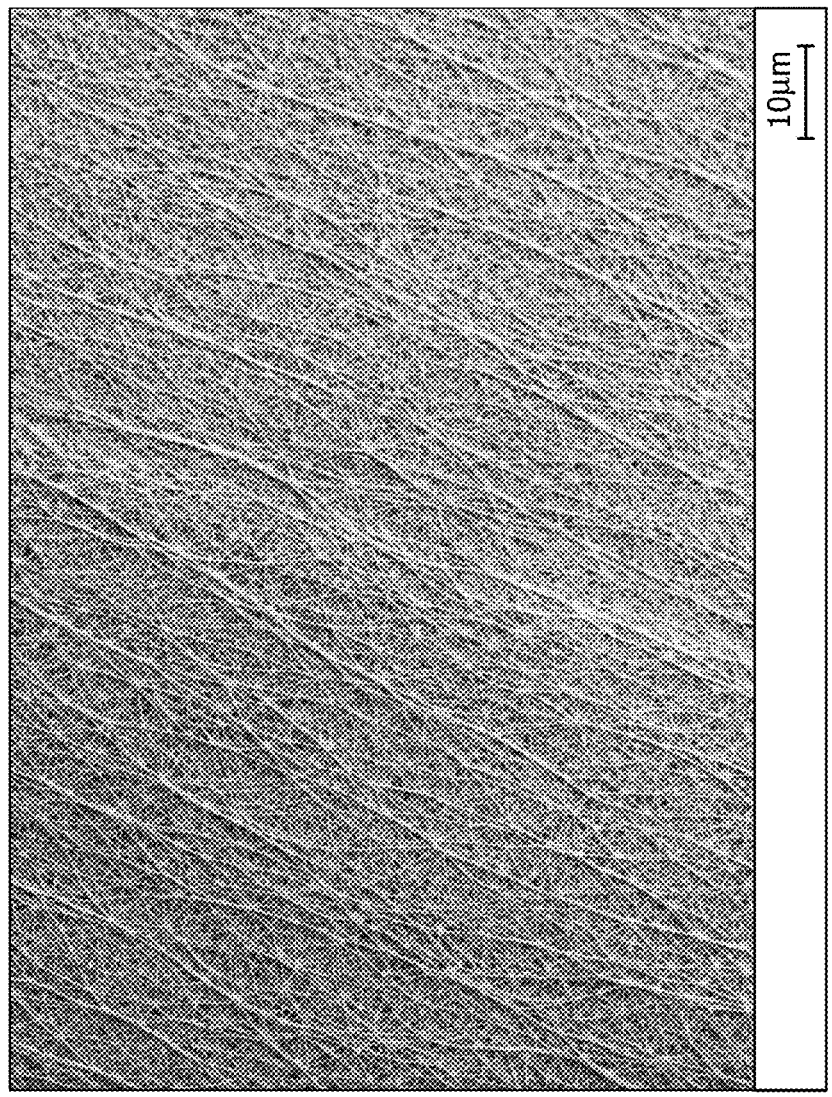
FIG. 2 is a scanning electron photomicrograph of the ePTFE side of an FEP-coated ePTFE film used to make devices described herein.

FIG. 2 is a scanning electron photomicrograph of the ePTFE side of a FEP-coated ePTFE film used to make devices described herein, using FEP-coated ePTFE film as described above.

Figure 3:
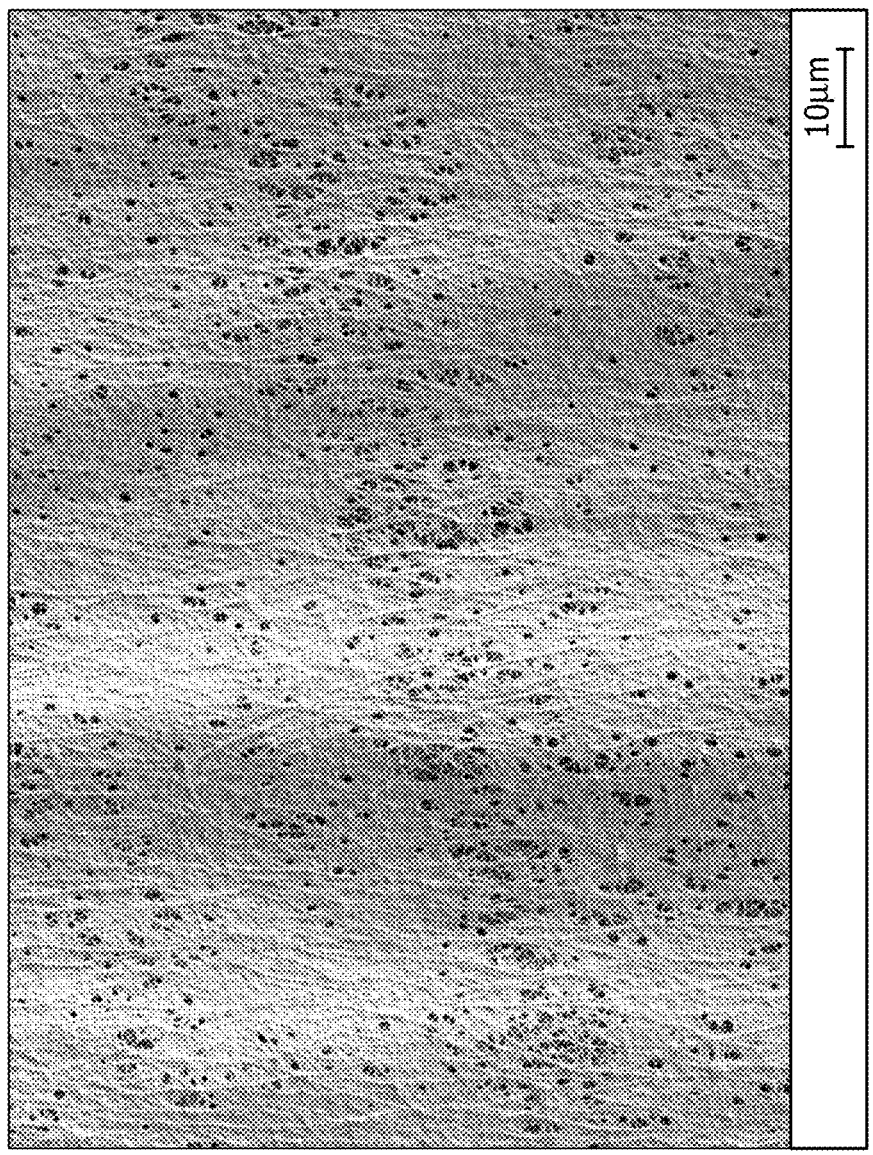
FIG. 3 is a scanning electron photomicrograph of the FEP coated side of the FEP-coated ePTFE film used to make devices described herein.

FIG. 3 is a scanning electron photomicrograph of the film shown in FIG. 2, showing the opposite, discontinuously FEP coated side of the FEP-coated ePTFE film.

Figure 4:
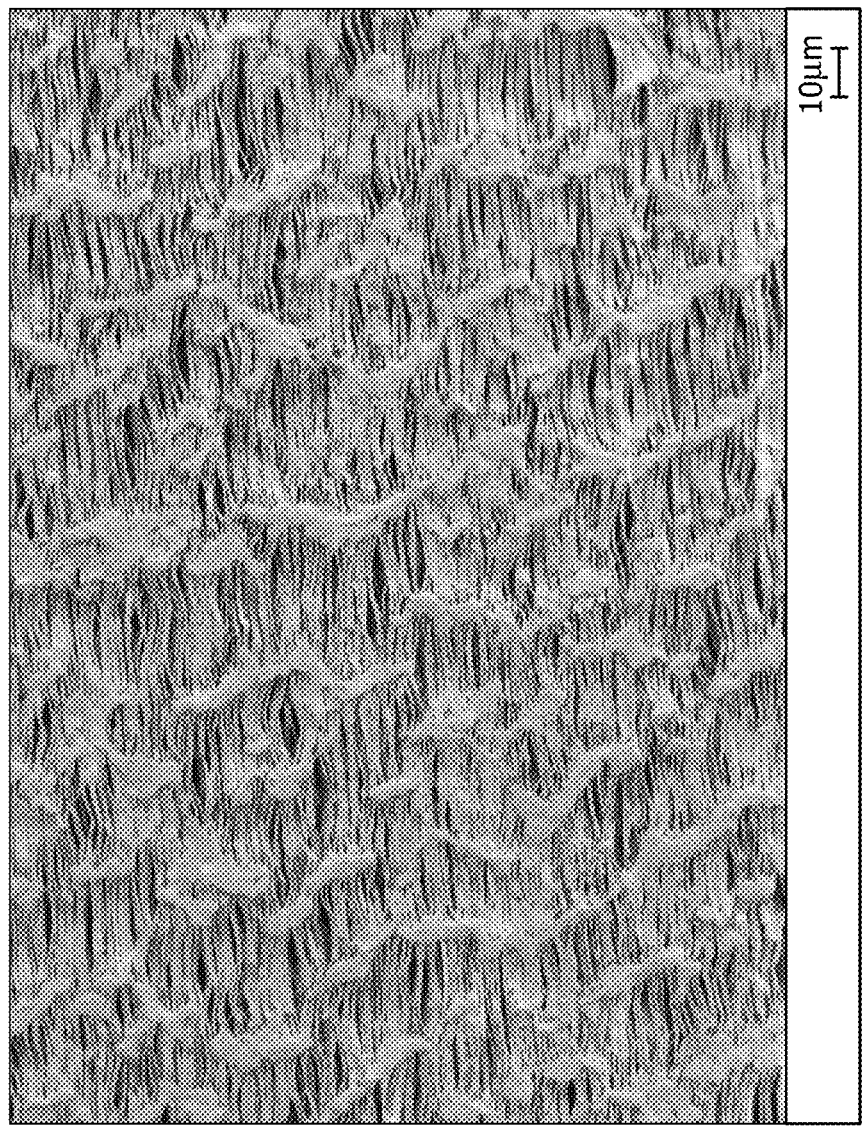
FIG. 4 is a scanning electron photomicrograph of the luminal surface of a 6 mm inside diameter ePTFE substrate tube as used to make a stent-graft described herein.

FIG. 4 is a scanning electron photomicrograph of the luminal surface of a 6 mm inside diameter ePTFE substrate tube as used to make a stent-graft described herein.

Figure 5:
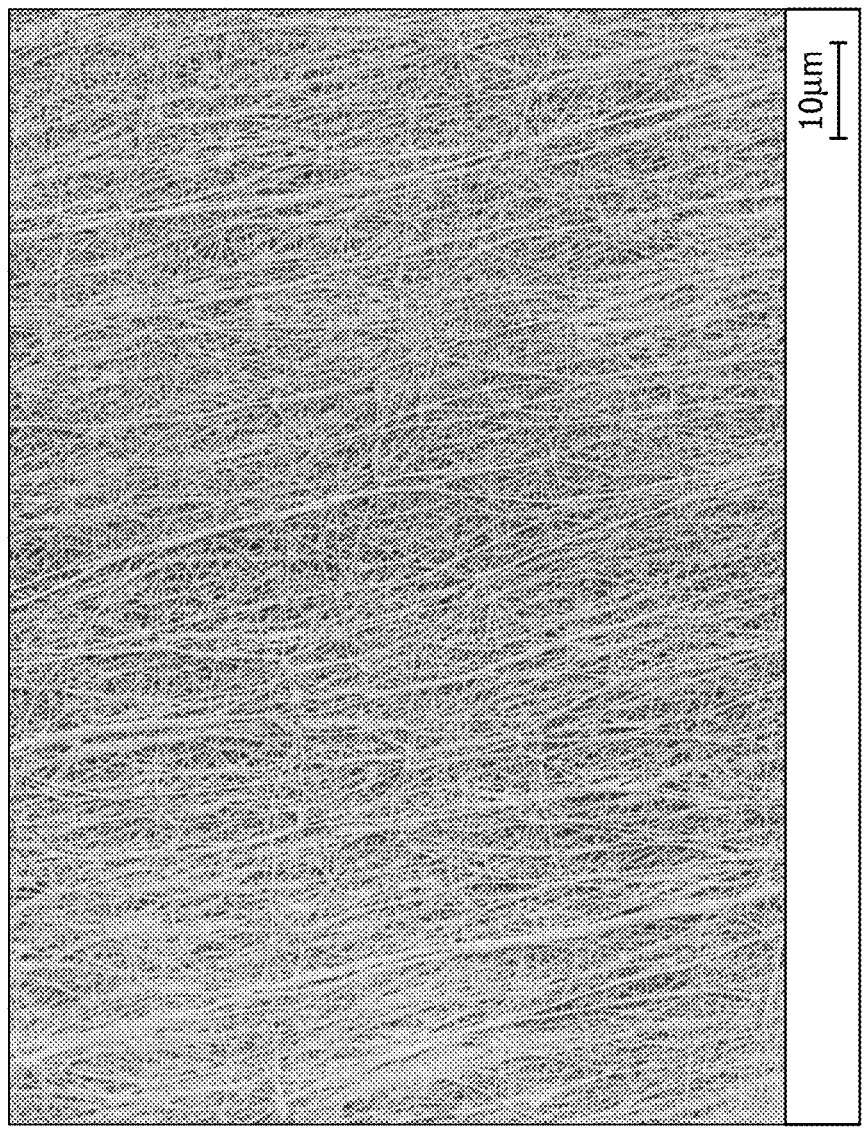
FIG. 5 is a scanning electron photomicrograph of the abluminal surface of the ePTFE substrate tube of FIG. 4 that has been helically wrapped with the FEP-coated ePTFE film applied with the FEP facing the substrate tube.

FIG. 5 is a scanning electron photomicrograph of the abluminal surface of the ePTFE substrate tube of FIG. 4 that has been helically wrapped with the FEP-coated ePTFE film applied with the FEP facing the substrate tube.

Figure 6:
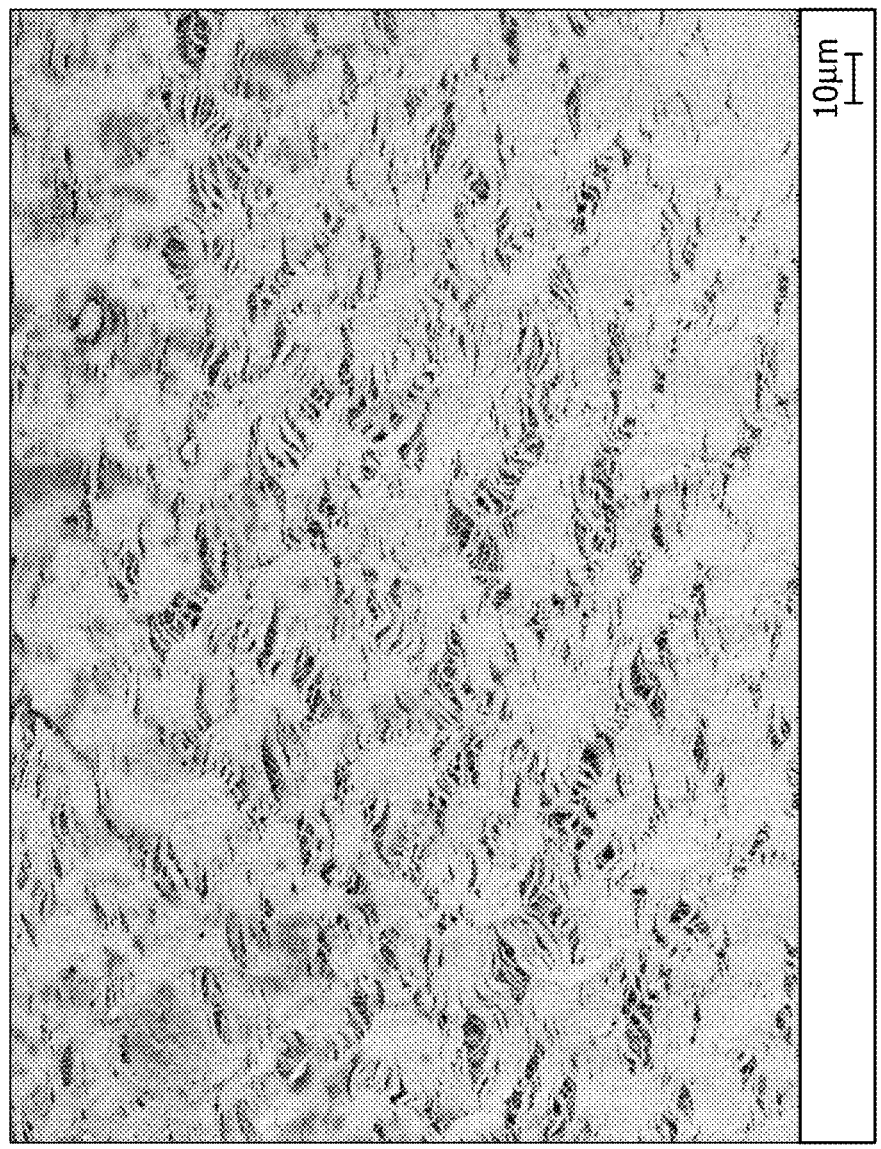
FIG. 6 is a scanning electron photomicrograph of the luminal surface of an ePTFE substrate tube as used to make a stent-graft described herein, following compaction of the stent-graft (with radial compression and heat) to an inside diameter of 4 mm.

FIG. 6 is a scanning electron photomicrograph of the luminal surface of an ePTFE substrate tube as used to make a stent-graft described herein, following compaction of the stent-graft (with radial compression and heat) to an inside diameter of 4 mm.

Figure 7:
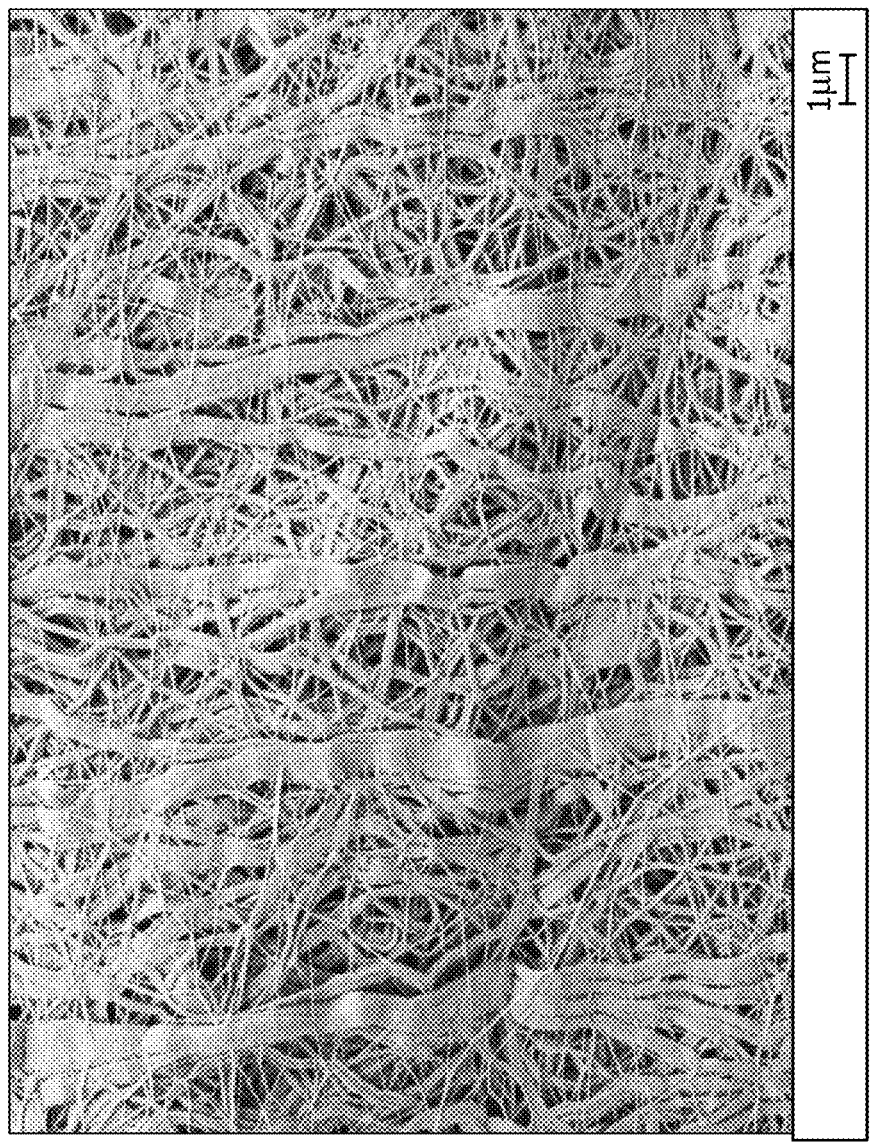
FIG. 7 is a scanning electron photomicrograph of the abluminal surface of the ePTFE substrate tube as used to make a stent-graft described herein, following compaction (with radial compression without applied heat (atypical, for illustration only)) to an inside diameter of 4 mm, showing that the FEP has not interpenetrated through the ePTFE film to the outer surface of that film.

FIG. 7 is a scanning electron photomicrograph of the abluminal surface of the film-wrapped ePTFE substrate tube as used to make a stent-graft described herein, following compaction (with radial compression without applied heat (atypical, for illustration only)) to an inside diameter of 4 mm, showing the bent fibrils of the film and showing that the FEP has not interpenetrated through the ePTFE film to the outer surface of that film.

Figure 8:
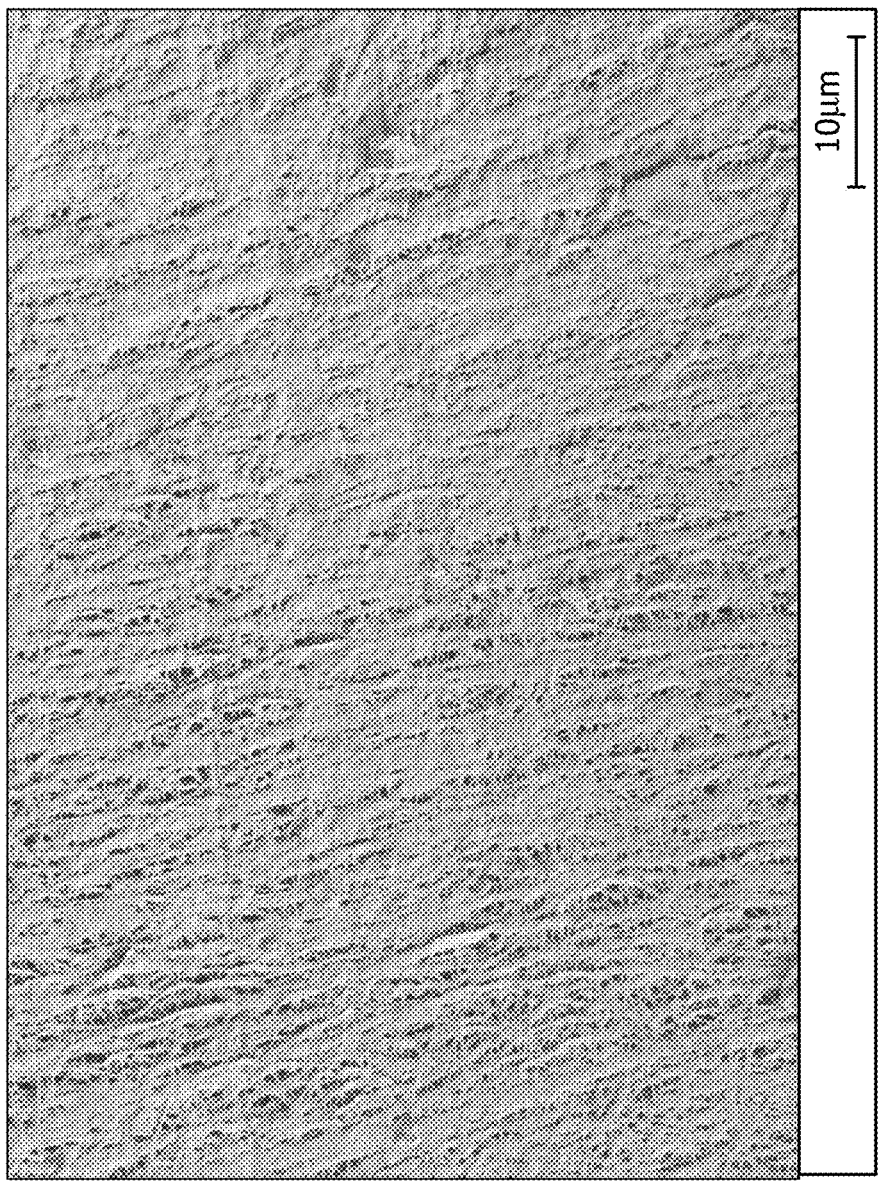
FIG. 8 is a scanning electron photomicrograph of the abluminal surface of the ePTFE substrate tube as used to make a stent-graft described herein, following compaction (with radial compression and with applied heat (typical)) to an inside diameter of 4 mm, showing the interpenetration of the FEP through the ePTFE film to the outer surface of that film.

FIG. 8 is a scanning electron photomicrograph of the abluminal surface of the film-wrapped ePTFE substrate tube as used to make a stent-graft described herein, following compaction (with radial compression and with applied heat (typical)) to an inside diameter of 4 mm, showing the interpenetration of the FEP through the ePTFE film to the outer surface of that film.

Figure 9:
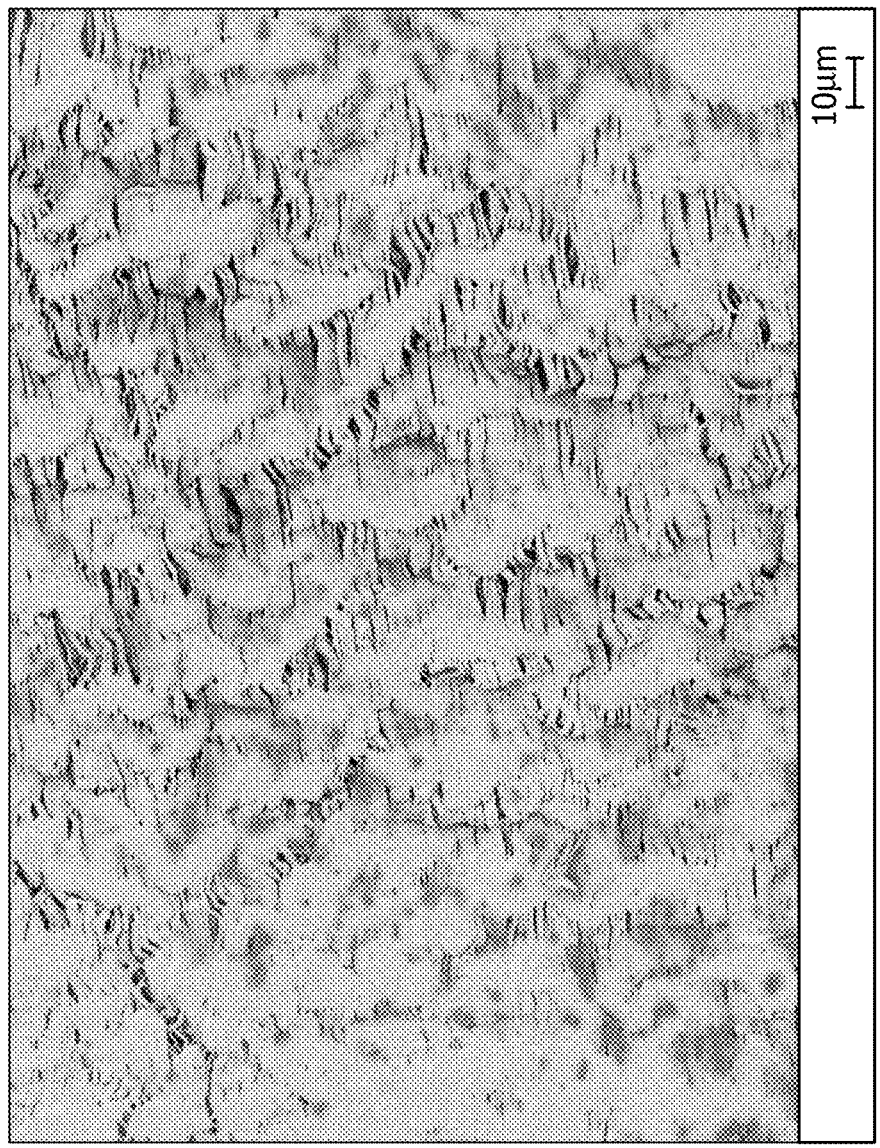
FIG. 9 is a scanning electron photomicrograph of the luminal surface of an ePTFE substrate tube as used to make a stent-graft described herein, following compaction of the stent-graft (with radial compression and heat) to an inside diameter of 4 mm in turn followed by expansion of the stent-graft with a catheter balloon to an inside diameter of 6 mm.

FIG. 9 is a scanning electron photomicrograph of the luminal surface of an ePTFE substrate tube as used to make a stent-graft described herein, following compaction of the stent-graft (with radial compression and heat) to an inside diameter of 4 mm in turn followed by expansion of the stent-graft with a catheter balloon to an inside diameter of 6 mm.

Figure 10:
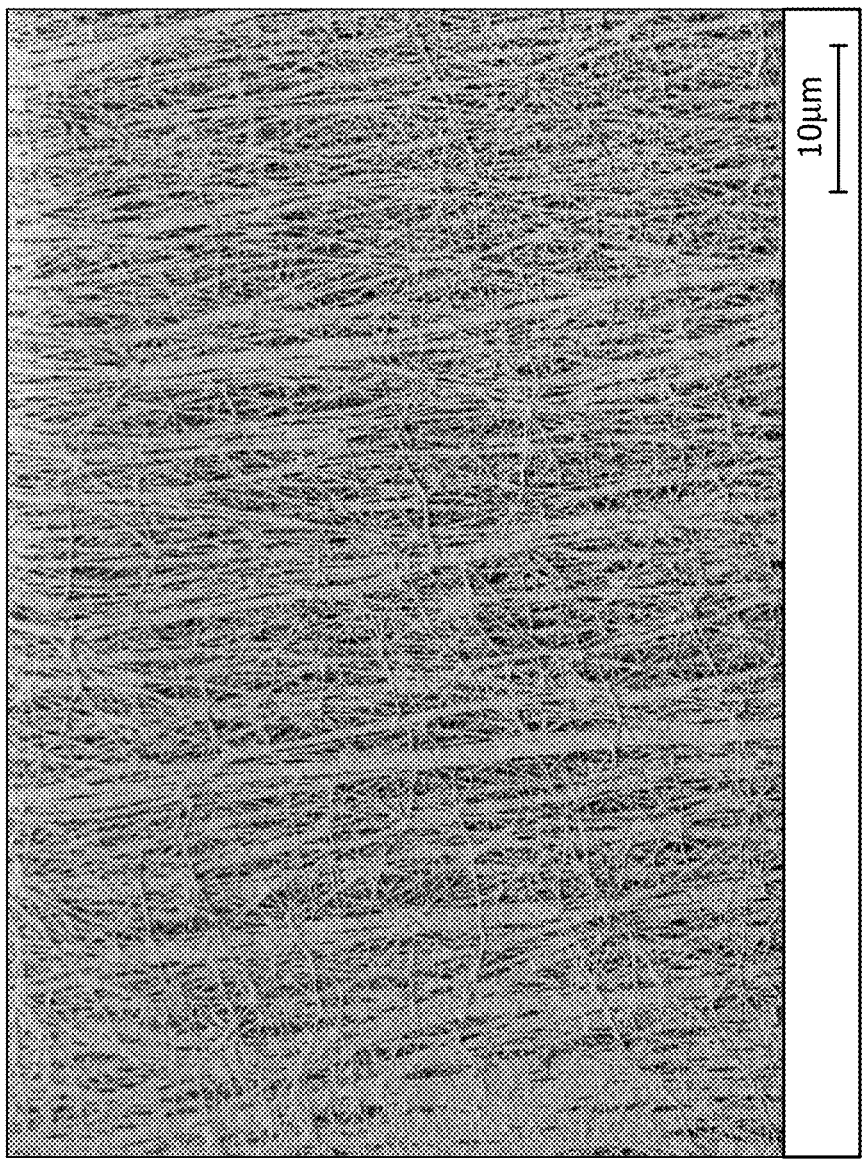
FIG. 10 is a scanning electron photomicrograph of the abluminal surface of the stent-graft shown in FIG. 9.

FIG. 10 is a scanning electron photomicrograph of the abluminal surface of the stent-graft shown in FIG. 9.

EXAMPLE 1

Diametrically Adjustable Vascular Graft

Figure 11:
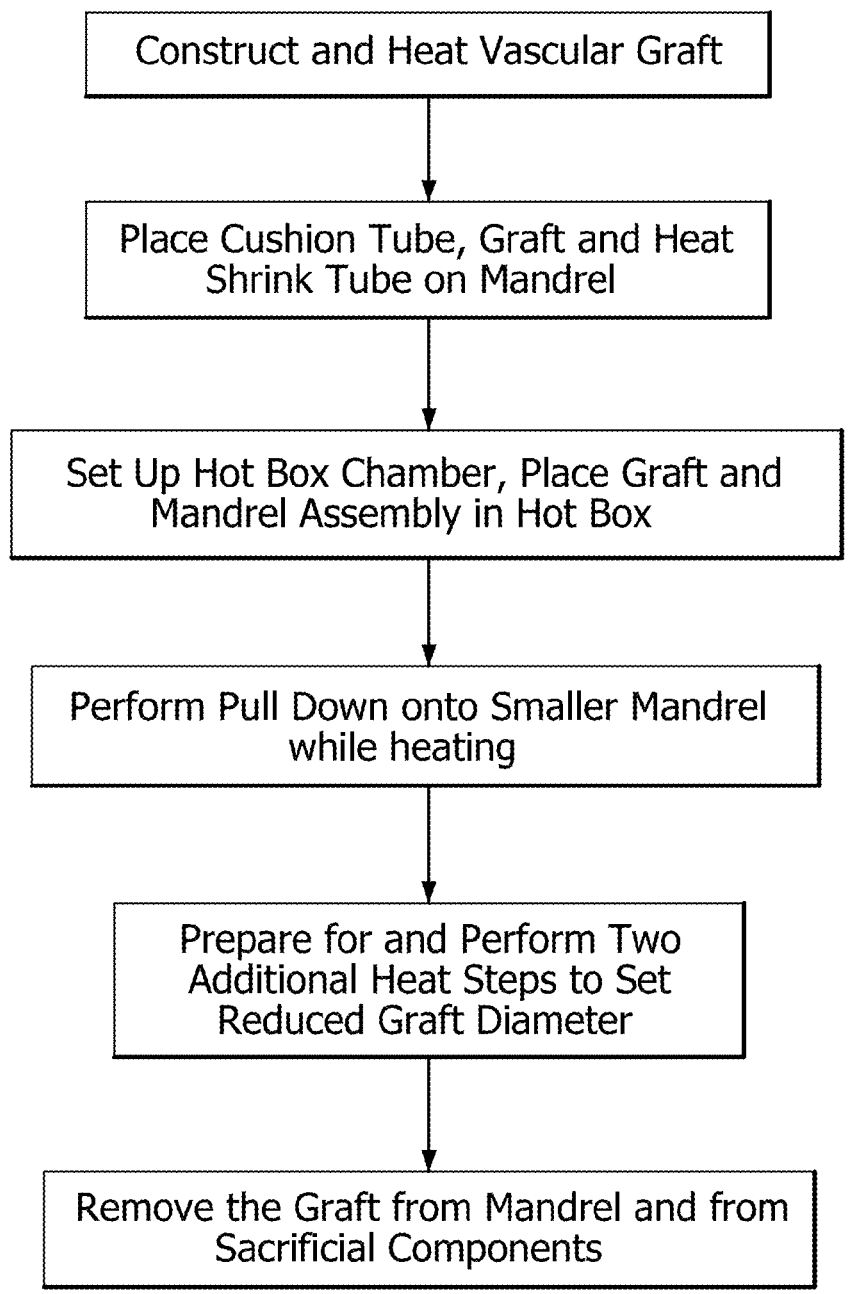
FIG. 11 describes a flow chart for the basic steps involved in the manufacture of a diametrically extensible ePTFE vascular graft.

The following is a description of a method used to make a diametrically extensible vascular graft that may be increased in diameter by inflation of a catheter balloon placed temporarily within the lumen of the vascular graft. The method described for making of the balloon extensible vascular graft is similar to a method described below for making of a balloon extensible stent-graft. The example of the vascular graft described herein was made to be diametrically extensible from a 4 mm inside diameter to a 6 mm inside diameter; larger ranges of extensibility are possible. A flow chart summary of this manufacturing process is described by FIG. 11.

First, a longitudinally extruded and expanded ePTFE tube was obtained, the tube having a 6 mm inside diameter, 15 cm length, 0.6 mm wall thickness and approximate 22 micron mean fibril length. This tube was fitted over a 6 mm outside diameter (OD) stainless steel mandrel. The tube was then provided with a helical wrap of 4 layers of 12.7 mm wide film of the type described above, with the FEP-coated side of the film against the outer surface of the ePTFE tube. Many of the fibrils of the film were thus substantially circumferentially oriented with respect to the mandrel and the ePTFE substrate tube.

The assembly was placed in a convection oven set at 320° C. for 20 minutes. This was sufficient heat to cause the FEP coating on the film to begin to melt, resulting in adhesion of the film to adjacent film layers and to the underlying ePTFE substrate tube, thereby creating, for purposes of this description, a vascular graft.

Next, a 6 mm OD tubular stainless steel mandrel was obtained, the mandrel having a 4 mm inside diameter (ID) and a slight (4°) taper (measured from the longitudinal axis of the mandrel) from the OD to the ID on one end. A 4 mm OD mandrel was inserted into the tapered end of the 6 mm mandrel, the 4 mm mandrel being sized to be a slip fit within the lumen of the 6 mm mandrel. (Alternatively, an adjustable diameter mandrel may be used.) A sacrificial thin wall ePTFE 5 mm ID cushion tube (30 cm length, 0.1 mm wall thickness, approximate 22 micron mean fibril length) was fitted onto the 6 mm mandrel with one end extending beyond the tapered end of the 6 mm mandrel about 5 cm onto the 4 mm mandrel. The previously created vascular graft was then fitted onto the 6 mm mandrel over the cushion tube, about 3 cm back from the taper. A length of sacrificial FEP shrink tube (Zeus Industrial Products, Inc., Orangeburg S.C.) having about a 1.6:1 ratio of expanded to retracted diameter was then fitted over the graft, the shrink tube being sized for clearance over the graft and having a length greater than that of the graft. The various components fitted onto the mandrel comprise the "assembly" that was subsequently processed.

A cylindrical hot box chamber of about 2.5 cm length with opposing round openings of about 9.5 mm on the entrance and 7.9 mm on the exit was attached to a heat source (Balloon Development Station Model 210-A, Beahm Designs, Los Gatos Calif.) set to 240° C. The opening sizes of the hot box chamber were chosen to provide clearance over the assembly on the 6 and 4 mm mandrels respectively. The tapered end of the 6 mm mandrel was placed in the center of the hot box chamber with the 4 mm mandrel extending out of the smaller chamber end. The location of the 6 mm mandrel was fixed in order to keep the tapered end of the 6 mm mandrel centered in the hot box.

The cushion tube and the 4 mm mandrel were grasped and both were pulled together through the hot box. Pulling was accomplished at a rate appropriate to shrink the FEP shrink tube tightly as it moved down the taper. As the vascular graft and shrink tube entered the chamber, the shrink tube collapsed onto the outside of the vascular graft. The graft moved down the taper onto the 4 mm mandrel, contained on the inside by the taper and on the outside by the shrink tube as it continued to reduce in diameter. This resulted in the microscopic bending of the fibrils in the helically wrapped film while avoiding macroscopic folding of the graft.

Following shrinking of the heat shrink tubing onto the vascular graft assembly and the 4 mm mandrel, the assembly was heated in a convection oven set at 210° C. for 10 minutes. This step was intended to heat set the bent fibrils. Next, the FEP shrink tubing was removed from the assembly. The vascular graft was then helically overwrapped with a sacrificial layer of 0.13 mm thick skived PTFE tape (St. Gobain Performance Plastics, Paris, France), after which the ends of the sacrificial ePTFE cushion tube extending beyond the ends of the vascular graft were cut off using a sharp blade. The assembly still on the 4 mm mandrel was placed in a convection oven set at 320° C. for ten minutes, causing the FEP coating on the ePTFE film to melt and flow into and at least partially through the bent fibrils of the film.

The graft assembly was then removed from the 4 mm mandrel, and the sacrificial skived PTFE wrapping and cushion tube were then removed from the vascular graft. Due to the FEP bonds holding the fibrils in the wrapped film in their bent configuration, the graft thus prepared remained at 4 mm ID until an internal force was introduced to increase its diameter. To test the graft, a 6 mm catheter balloon attached to a balloon inflator via its catheter was inserted into the graft and inflated. The graft gradually increased in diameter until returned to its original 6 mm diameter at about 7 atmospheres of balloon inflation pressure.

EXAMPLE 2

Self Expanding/Balloon Adjustable Stent-Graft

A 4 mm covered stent-graft with a self expanding nitinol wire stent (a helically wound serpentine wire form) that can be subsequently extended in diameter (e.g., with a catheter balloon) to 6 mm was made as described below; this stent-graft is illustrated in FIG. 1 which shows a portion of the stent-graft having been balloon expanded to an ID of 6 mm.

An ePTFE tube was obtained, the tube having a 6 mm ID, about 8 cm length, bulk density of about 0.6 g/cc, 0.1 mm wall thickness and approximate 22 micron mean fibril length. This tube was fitted over a 6 mm OD stainless steel mandrel, then wrapped with FEP-coated ePTFE film and heated as described above for the example of the diametrically extensible vascular graft. The graft was then removed from the 6 mm OD stainless steel mandrel. An ePTFE sacrificial cushion tube as described previously was fitted onto a 6 mm OD porous stainless steel mandrel, after which the film-wrapped ePTFE graft was fitted over the cushion tube.

A helically wound wire stent was obtained and then fitted over the center of the length of the film-wrapped ePTFE tube at a stent length of about 5 cm. 1 mm wide FEP-coated film, about 0.01 mm FEP thickness, about 0.035 mm total thickness, bulk density about 1.2 g/cc was then wrapped over the length of the helically wound wire, centered on the width of the serpentine form so that the apices of the serpentine form remained exposed. A 12.7 mm wide strip of this film was then wrapped circumferentially around each end of the device covering about the last three windings of the helical wire form. This film extended beyond the end of the stent. An overwrapping of sacrificial skived PTFE tape was then applied over the entire length of the stent. The resulting assembly was then placed into a convection oven set at about 320° C. A vacuum was applied to the lumen of the porous mandrel and the assembly was left in the oven to heat for 10 minutes, after which the assembly was removed and allowed to cool to about ambient temperature.

The resulting graft was removed from the 6 mm porous mandrel and the cushion tube removed from the lumen of the now-formed stent-graft. The stent-graft was then fitted onto another 6 mm OD stainless steel mandrel and the film protruding beyond the ends of the stent was trimmed with a laser (Blockwise Engineering, Tempe Ariz.) to conform to the serpentine wire. The trimmed stent-graft was then removed from the 6 mm mandrel.

A 6 mm mandrel having one tapered end and including a 4 mm OD mandrel inserted into the tapered end of the lumen of the 6 mm mandrel was obtained, (this mandrel previously described above). A sacrificial ePTFE inner cushion tube (also as the previously described cushion tube) was fitted onto the 6 mm mandrel, extending about 5 cm onto the 4 mm mandrel. The stent-graft was then fitted over the portion of the cushion tube covering the 6 mm mandrel to about 3 cm from the beginning of the taper.

A sacrificial helical wrapping of skived PTFE tape (St. Gobain Performance Plastics, Paris, France) was then applied over the stent-graft. A sacrificial ePTFE crush tube about 0.25 mm thickness with a density of about 0.75 g/cc and fibril length of about 30 microns was placed over the skived tape layer and crushed into the interstices of the stent using a Blockwise Model G iris style crusher (Blockwise Engineering, Tempe Ariz.), thus compacting the stent-graft into contact with the underlying ePTFE sacrificial cushion tube. A sacrificial FEP shrink tube (Zeus Industrial Products, Inc., Orangeburg S.C.), with an expanded diameter of about 7 mm, retracted diameter of about 4 mm and a wall thickness of about 0.5 mm, was placed over the sacrificial ePTFE crush tube. Finally, a sacrificial 7.5 mm ID ePTFE outer cushion tube was fitted over the entire assembly and over the full length of the inner ePTFE cushion tube, this cushion tube being the same as previously described cushion tubes except for the ID.

The tapered portion of the 6 mm mandrel was inserted into a hot box chamber about 5.1 cm long, 2.5 cm in diameter, with openings in the entrance to provide some clearance for the outside diameter of the outer cushion tube before retraction (about 7.6 mm diameter) and at the exit to accommodate the outside diameter of the outer cushion tube over the shrink tube after retraction (about 6.4 mm diameter).

Figure 12:
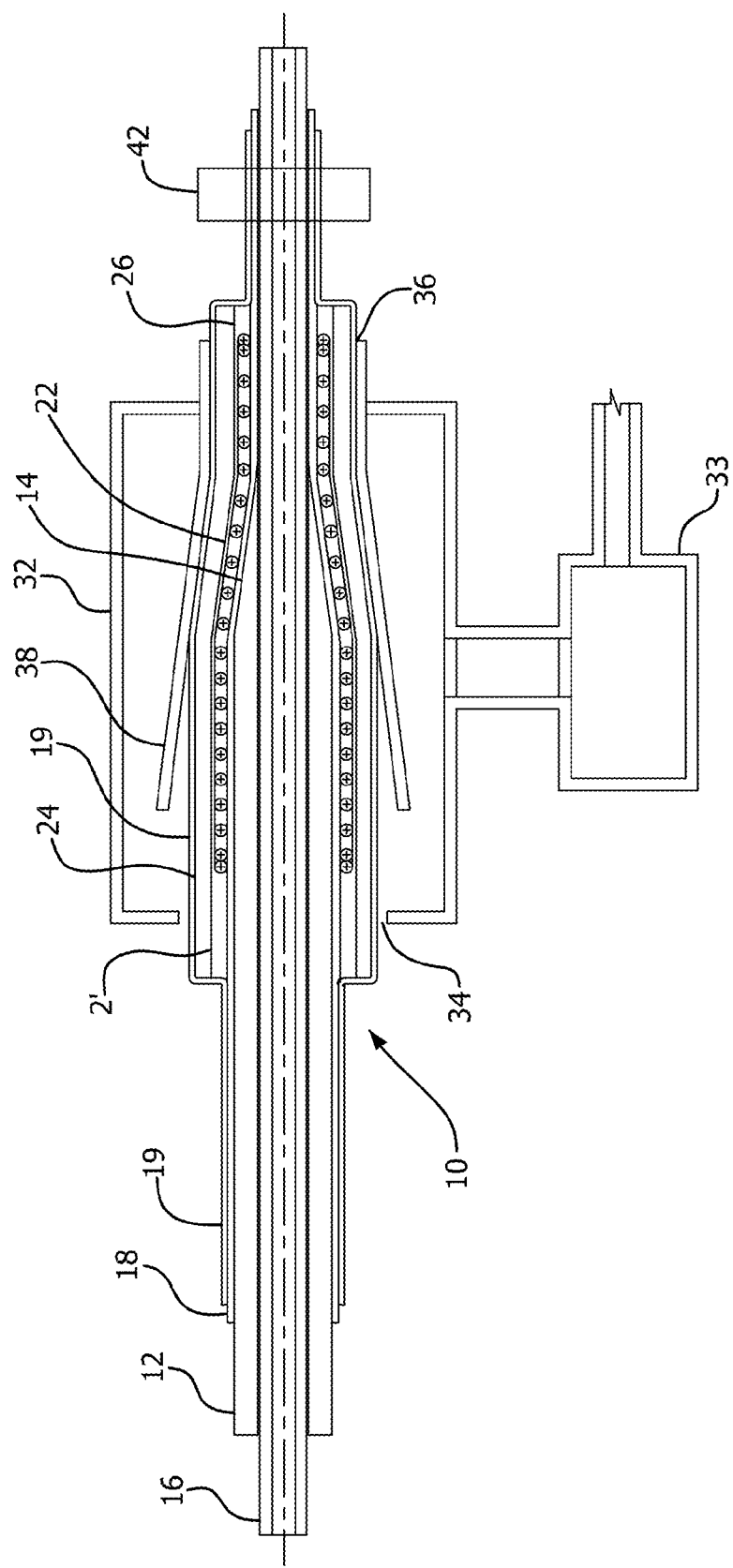
FIG. 12 is a longitudinal cross sectional view of the hot box chamber used for manufacturing of a diametrically extensible stent-graft.

FIG. 12 is a longitudinal cross section of the hot box chamber 32 showing the mandrel and graft assembly 10 as inserted into the hot box chamber 32 in the process of pulling the graft assembly 10 down from the 6 mm mandrel 12, and across the taper 14 of the 6 mm mandrel 12 (and between taper 12 and funnel 38 within hot box chamber 32; funnel 38 is unique to this example) onto the 4 mm mandrel 16. Funnel 38 is required to have the same 4° taper as the taper at the end of the 6 mm mandrel; the spacing between the taper 14 of the 6 mm mandrel and the funnel 38 should be appropriate to accommodate the thickness of the graft assembly 10. The hot box chamber 32 was attached to a heat source 33 (Balloon Development Station Model 210-A, Beahm Designs, Los Gatos Calif.) set to 240° C.

The graft assembly 10 was pulled through the entrance 34 to the hot box chamber 32, the chamber funnel 38, and chamber exit 36 by gripping clamp 42 and pulling the exposed end of the inner 18 and outer 19 cushion tubes onto the 4 mm mandrel 16. The graft assembly 10 was thus moved from the 6 mm mandrel 12, across the mandrel taper 14 (and through funnel 38), onto the 4 mm mandrel 16. As the shrink tube 24 entered the chamber 32 it shrank down onto the outside of the crush tube 26, thus holding the graft tightly against the mandrels 16, 12 and taper 14, causing the stent-graft 22 ID to be reduced to 4 mm without visibly wrinkling the luminal surface of the stent-graft 22. The fibrils in the FEP-coated ePTFE film wrapping of the stent-graft 22 were bent circumferentially and mingled with the FEP. The process was continued until the full length of the stent-graft 22 was pulled down onto the 4 mm mandrel 16, with the assembly 10 being fully removed from hot box 32.

The outer cushion tube 19 was removed and the remaining assembly 10 was removed from the 4 mm mandrel 16. The inner cushion tube 18 was then removed. The remaining assembly 10 was placed onto another 4 mm mandrel (not shown). The assembly was placed in a Blockwise Model G iris style crusher (Blockwise Engineering, Tempe Ariz.); crusher set points were 100° C. and 120 psi. Electrodes attached to a Magna-Power Electronics DC power supply, model XR10-200 (Magnapower Electronics, Flemington, N.J.), were attached to the mandrel. One hundred amps at about 2 volts was conducted through the mandrel and the graft assembly, causing the FEP coating on the ePTFE film to melt and flow into and at least partially through the bent fibrils of the film. Following the conclusion of the heating process, the crush pressure was released and the assembly was removed from the crusher. The shrink tube and crush tube were removed from the stent-graft, which was then removed from the mandrel.

The completed, diametrically compacted device can be returned to its original 6 mm diameter, or any diameter in-between, by the application of an inflating catheter balloon force to the luminal surface. Typically about 8-9 ATM of force is required to return the device to its full diameter.

The device thus manufactured can be loaded onto a catheter delivery system through a fluted metal funnel as described in U.S. Pat. No. 6,702,845 to Cully et al., and inserted into a remotely removable covering as described in U.S. Pat. No. 6,224,627 to Armstrong et al. The device can then be delivered to a selected vessel location, deployed by releasing the device from the covering, and ballooned as appropriate to fit the vessel. The resulting device will be substantially wrinkle free across its usable range and can be custom fitted to the ID of the vessel by the clinician appropriately to fit the vessel's anatomy.

EXAMPLE 3

Length Adjustable Vascular Graft

A length adjustable 6 mm vascular graft was produced by making an about 25 cm long vascular graft in the method described above for the diametrically extensible graft. The graft was then placed on a 6 mm stainless steel mandrel, and then compressed longitudinally to a length of about 7.5 cm, or about 30% of its original length. In the process, the fibrils in the graft including the fibrils of the film become bent. The graft on the mandrel was placed in a 320° C. convection oven for 10 minutes. During this process the FEP on the film of the graft was melted and flows into the void spaces between the bent fibrils. After removal from the oven and cooling to about ambient temperature, the graft was removed from the mandrel. The length of the graft thus shortened was about 50% less than the original length. The FEP mingled with the bent fibrils retains the graft in its shortened length until it was manually extended by the application of a tensile force up to about its original precursor length. Some degree of foreshortening of the graft was observed, however the graft retained at least 90% of the length of the precursor tube after extension.

Examples 2 and 3 can be combined to make a graft that is length and diameter adjustable. The graft should be reduced in length first as described in Example 2, then can be made diameter adjustable using the process in Example 3.

EXAMPLE 4

Diametrically Extensible Tube Having Bent Nodes

Figure 13:
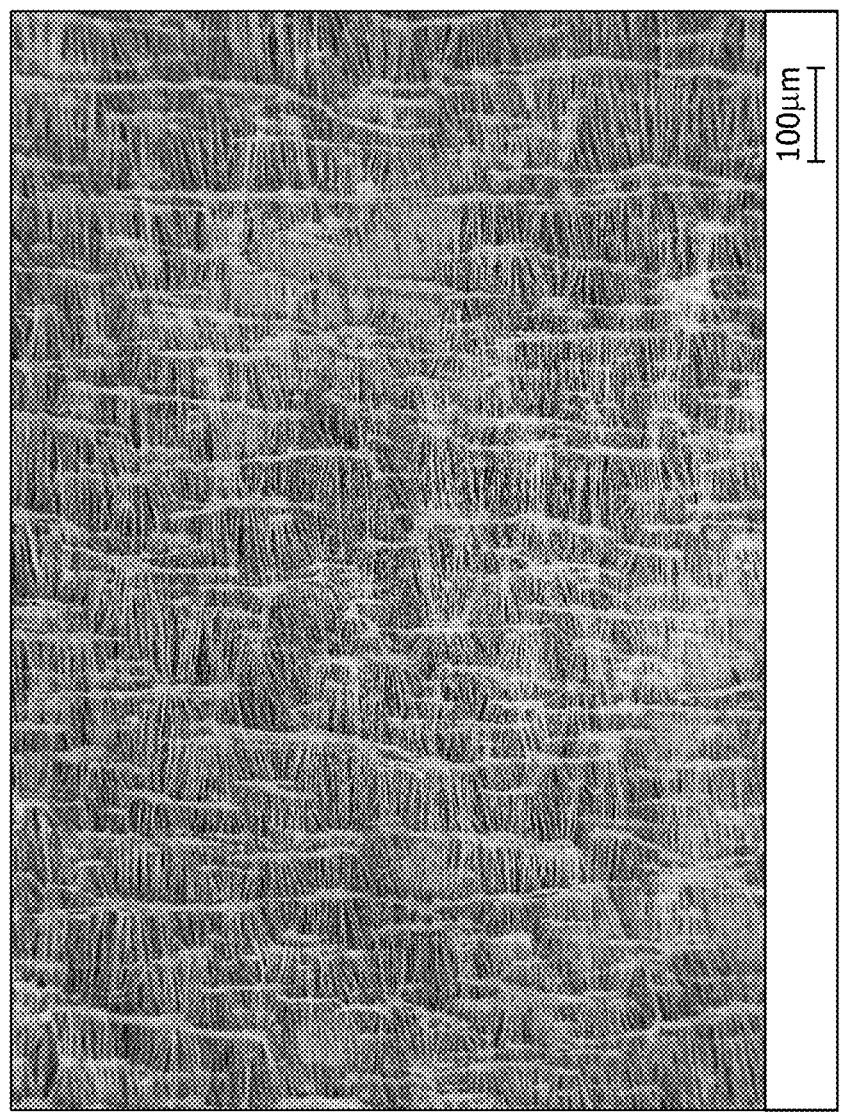
FIG. 13 is a scanning electron photomicrograph of an ePTFE film having a microstructure of nodes interconnected by fibrils.

A 4 mm ID tube with bent nodes to provide diametric adjustability out to 6 mm ID was produced using an ePTFE film with an area weight of about 5 g/m². The film, about 0.01 mm thickness, bulk density about 0.2 g/cc, having a microstructure of longitudinally oriented fibrils averaging about 80 micron average fibril length, and transversely oriented nodes averaging about 200 microns in length. A sample of this material is shown in FIG. 13. A sample of the film, 25 cm long and 8 cm wide, with the fibrils oriented longitudinally and nodes oriented circumferentially, was cigarette wrapped onto a 6 mm mandrel, yielding a tubular wrap 25 cm long with about 5 layers of the film. The tubular wrap was radially overwrapped with a sacrificial layer of Kapton slit to form a 2.5 cm wide tape to provide a compressive outer force. This tubular composite was then heated to 380° C. for 12 minutes to form a film tube. The Kapton wrap was removed and discarded. The resulting film tube was then removed from the mandrel.

A mandrel was procured having a 6 mm diameter for a portion of its length, and then tapering at an angle of 4° (the taper being measured off of the longitudinal axis of the mandrel), down to a 4 mm diameter for the remainder of the length of the mandrel. A 40 cm long 5 mm diameter sacrificial cushion tube as described previously, was fitted over the 6 mm diameter portion of the mandrel and extended 10 cm onto the 4 mm mandrel. The film tube was fitted over the cushion tube on the 6 mm portion of the mandrel about 3 cm back from the taper. A 12.7 mm wide strip of 1.5 mm thick sacrificial silicone strip 60 cm long was wrapped tightly around the sintered tube. The cushion tube was then grasped along the 4 mm portion of the mandrel and was used to pull the wrapped film tube down the taper onto the 4 mm mandrel. In the process, the film tube was contained by the taper on the inside and the tightly wrapped silicone strip on the outside. The result was that the circumferentially oriented nodes were bent microscopically while the film tube diameter was reduced from 6 to 4 mm, macroscopically wrinkle free.

Figure 14:
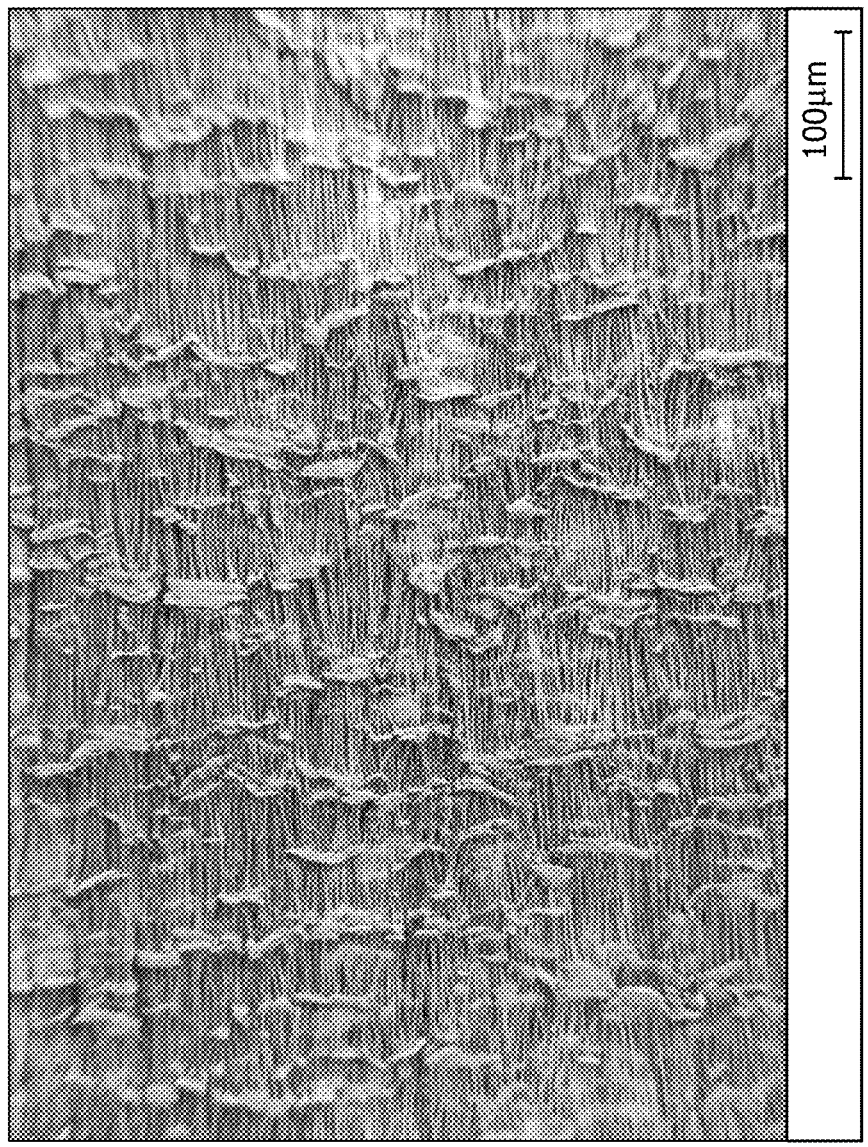
FIG. 14 is a scanning electron photomicrograph of an ePTFE film having a microstructure of nodes interconnected by fibrils (per FIG. 13), taken after the application of compression to the film in the direction of the length of the nodes, resulting in folding of the nodes (i.e., bent nodes).
Figure 15:
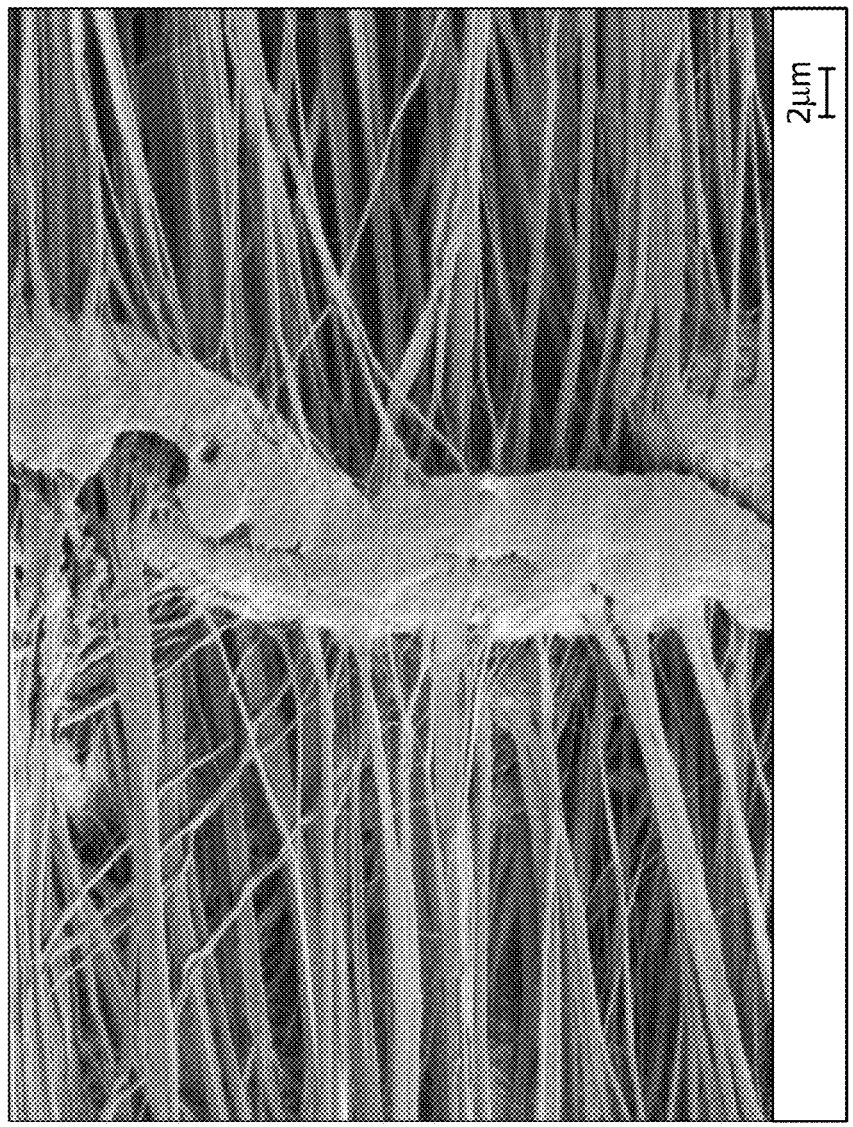
FIG. 15 is a scanning photomicrograph of a bent node that has been folded back on itself.

The assembly was placed in a 210° C. convection oven for 10 minutes to begin to set the bent form of the nodes. The silicone strip was then removed and a sacrificial layer of 0.012 mm skived PTFE (St. Gobain Performance Plastics, Paris, France) was tightly wrapped over the film tube. The film tube was placed in a 370° C. convection oven for 5 minutes, then removed and allowed to cool to ambient temperature. The skived PTFE tape was removed from the film tube, and then the film tube and cushion tube were removed from the mandrel and the cushion tube was removed from the ID of the film tube. The completed tube had bent nodes in the circumferential direction as shown in FIGS. 14 and 15.

Figure 16:
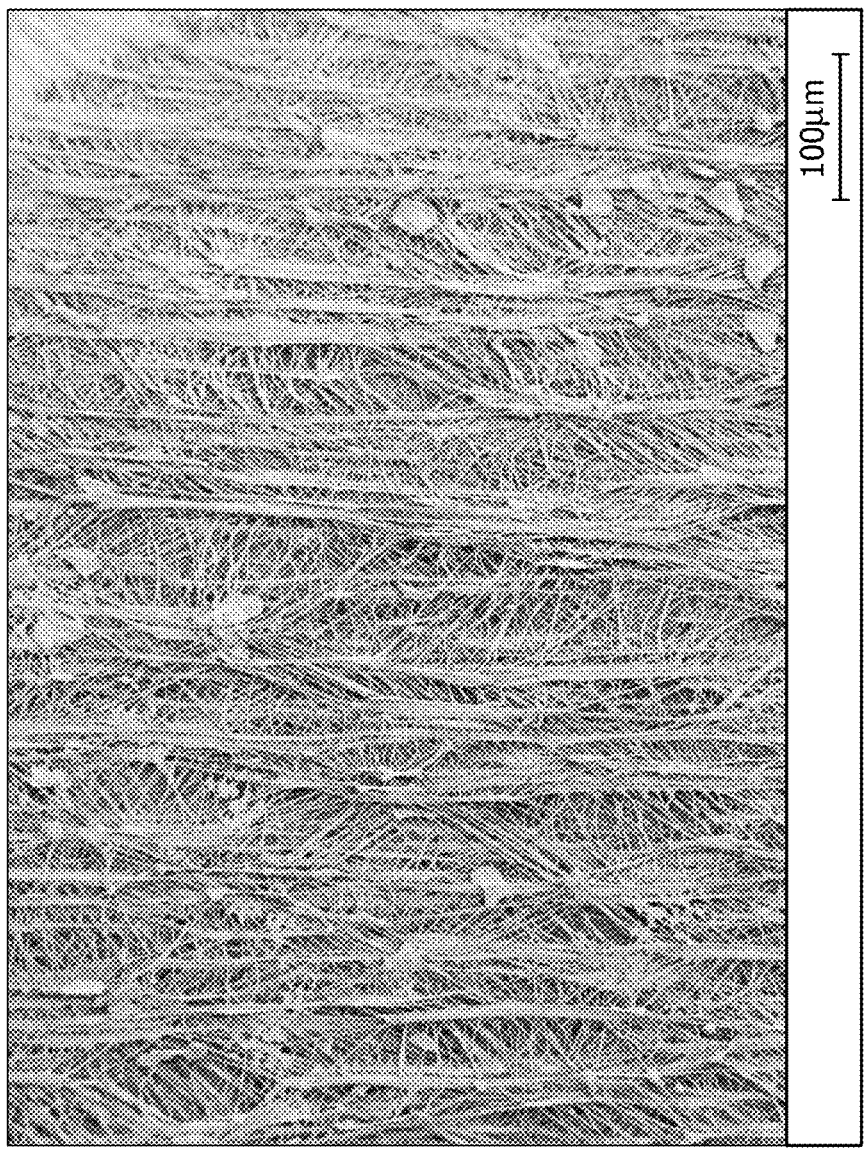
FIG. 16 is a scanning electron photomicrograph of an ePTFE film having a microstructure of nodes interconnected by fibrils, wherein the nodes have been folded per FIG. 14, following the application of a tensile force in the direction of the length of the nodes, sufficient to substantially straighten the nodes.

The film tube thus manufactured with bent nodes was placed on a 6 mm catheter balloon. The balloon was inflated and the film tube returned to its original 6 mm inside diameter. The nodes substantially returned to their original, unbent form as shown in FIG. 16.

For purposes of the present description, the average nodal length is determined by obtaining a photomicrograph of a surface of an ePTFE sample that shows a node and fibril microstructure at a magnification level that includes at least ten sequential nodes that intersect a line drawn across the length of the middle vertical region of the photomicrograph. The individual heights of ten sequential nodes taken beginning from left to right on the photomicrograph are determined by measuring with dividers referenced against a scale that accounts for the magnification factor. The ten heights are then averaged to provide the average nodal length.

Bent nodes will generally have an appearance of being substantially bent, i.e., bent in an amount of ninety degrees or more. These fibrils may be bent into 2 or 3 parallel segments (analogous to a letter U that has been flattened in a horizontal direction (e.g., similar to FIG. 15) or a letter Z that has been flattened in a vertical direction). More generally, bent nodes exist when, for a substantial portion of nodes within a given sample, at least 4 out of 10 nodes sampled from a photomicrograph as described above are determined to be bent in an amount of about 90 degrees of more.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

The invention claimed is:

1. An implantable article comprising a first material having a microstructure of fibrils wherein a substantial portion of said fibrils are in a substantially bent configuration and wherein a substantial portion of said bent fibrils are constrained in the substantially bent configuration by a coating of fracturable material applied to the first material that is different from the first material, wherein said article is adapted to be extended during normal use of said article in at least one dimension by a tensile force applied in a direction to cause fracturing of the fracturable material and straightening of the bent fibrils.

2. An implantable article according to claim 1 wherein said first material is porous expanded polytetrafluoroethylene.

3. An implantable article according to claim 1 wherein said fracturable material is fluorinated ethylene propylene.

4. An implantable article according to claim 3 wherein said first material is porous expanded polytetrafluoroethylene.

5. An implantable article according to claim 1 wherein said article has a length, a width and a thickness and said dimension is a length dimension.

6. An implantable article according to claim 1 wherein said article is a tubular article and said dimension is a diameter of said tubular article.

7. An implantable article according to claim 6 wherein said tubular article is a vascular graft.

8. An implantable article according to claim 6 wherein said tubular article is a stent-graft.

9. An implantable article according to claim 6 wherein said tubular article may be extended in diameter by up to about 50%.

10. An implantable article according to claim 1 wherein said article is a tubular article and said dimension is a length of said tubular article.

11. An implantable article according to claim 10 wherein said tubular article is a vascular graft.

12. An implantable article according to claim 11 wherein said tubular article is extensible in length up to about 50%.

13. An implantable article according to claim 1 wherein said article is in the form of a sheet.

14. An implantable article according to claim 1 wherein said article is adapted to be extended in at least two directions.

15. An implantable article according to claim 14 wherein said article is a tubular vascular graft and said at least two directions are a length direction and a diameter direction.

16. An implantable material comprising a first material having a microstructure including a multiplicity of fibrils and having an average fibril length, wherein at least a portion of said fibrils are length constrained by a second material including a fracturable material coated on the first material that is not the same material as the first material, and wherein during normal use of the article, upon the application of a force to the article in a direction that is substantially parallel to the length of the fibrils, said average fibril length is significantly increased and remains significantly increased following removal of the force.

17. An implantable material according to claim 16 wherein said first material is porous expanded polytetrafluoroethylene.

18. An implantable material according to claim 16 wherein said second material is fluorinated ethylene propylene.

19. An implantable material according to claim 18 wherein said first material is porous expanded polytetrafluoroethylene.

20. An implantable material according to claim 16 wherein said first material has a length, a width and a thickness and the average fibril length is increased in a direction substantially parallel to the length of the material.

21. An implantable material according to claim 16 wherein said first material is a tubular material and the average fibril length is increased in a direction substantially parallel to a diameter of said tubular material.

22. An implantable material according to claim 21 wherein said tubular material is a vascular graft.

23. An implantable material according to claim 21 wherein said tubular material is a stent-graft.

24. An implantable material according to claim 21 wherein said tubular material may be extended in diameter by up to about 50%.

25. An implantable material according to claim 16 wherein said first material is a tubular material and the average fibril length is increased in a direction substantially perpendicular to a diameter of said tubular material.

26. An implantable material according to claim 25 wherein said tubular material is a vascular graft.

27. An implantable material according to claim 26 wherein said tubular material is extensible in length up to about 50%.

28. An implantable material according to claim 16 wherein said first material is in the form of a sheet.

29. An implantable material according to claim 16 wherein said first material is adapted to be extended in at least two directions.

30. An implantable material according to claim 29 wherein said first material is a tubular vascular graft and said at least two directions are a length direction and a diameter direction.

* * * * *